US011521747B2

(12) United States Patent
Chatterjee et al.

(10) Patent No.: US 11,521,747 B2
(45) Date of Patent: *Dec. 6, 2022

(54) LIBRARY SCREENING FOR CANCER PROBABILITY

(71) Applicant: International Business Machines Corporation, Armonk, NY (US)

(72) Inventors: Avijit Chatterjee, White Plains, NY (US); Wendy Wang, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 14 days.

This patent is subject to a terminal disclaimer.

(21) Appl. No.: 16/534,533

(22) Filed: Aug. 7, 2019

(65) Prior Publication Data

US 2019/0362854 A1    Nov. 28, 2019

Related U.S. Application Data

(63) Continuation of application No. 15/864,278, filed on Jan. 8, 2018, now Pat. No. 10,692,605.

(51) Int. Cl.
*G16H 50/30* (2018.01)
*G16H 50/50* (2018.01)
(Continued)

(52) U.S. Cl.
CPC .............. *G16H 50/30* (2018.01); *G06N 5/00* (2013.01); *G16H 10/60* (2018.01); *G16H 15/00* (2018.01); *G16H 50/20* (2018.01); *G16H 50/50* (2018.01)

(58) Field of Classification Search
CPC ... G06F 1/00–2221/2153; G16H 10/00–80/00; G06N 3/00–99/007
See application file for complete search history.

(56) References Cited

U.S. PATENT DOCUMENTS 6,344,316 B1    2/2002  Lockhart et al.
6,714,925 B1 *  3/2004  Barnhill ............... G06Q 10/10
                                          706/48
(Continued)

FOREIGN PATENT DOCUMENTS

CN     104541276     4/2015
CN     107203772     9/2017
(Continued)

OTHER PUBLICATIONS

SungHwan Kim, "Statistical Learning Methods for Multi-Omics Data Integration in Dimension Reduction, Supervised and Unsupervised Machine Learning," Submitted to the Graduate Faculty of the Department of Biostatistics of the Graduate School of Public Health, University of Pittsburgh, 2015 (Year: 2015).*

(Continued)

*Primary Examiner* — Jonathon A. Szumny
(74) *Attorney, Agent, or Firm* — Heslin Rothenberg Farley & Mesiti P.C.; Scott Dobson, Esq.

(57) ABSTRACT

A method, system, and computer program product are provided for generating a predictive model. A processor(s) obtains a raw data set (peptide libraries) of patients designated as diagnosed/pre-diagnosed with a condition or not diagnosed with the condition. The processor(s) segments the raw data set into a pre-defined number of groups and separates out a holdout group. The processor(s) performs a principal component analysis on the remaining groups to identify, based on a frequency of features in the remaining groups, common features (principal components) in the remaining groups and weighs the common features based on frequency of occurrence. The processor(s) determines a smallest number of the principal components that yields a pre-defined level of validation accuracy. The processor(s) generates a predictive model, by utilizing the smallest num- (Continued)

ber for a best fit in a logistic regression model. The predictive model provides binary outcomes.

8 Claims, 7 Drawing Sheets

(51) Int. Cl.
| | |
|---|---|
| *G06N 5/00* | (2006.01) |
| *G16H 10/60* | (2018.01) |
| *G16H 15/00* | (2018.01) |
| *G16H 50/20* | (2018.01) |

(56) References Cited

U.S. PATENT DOCUMENTS

| | | | |
|---|---|---|---|
| 9,702,011 | B2 | 7/2017 | Cox et al. |
| 10,692,605 | B2 | 6/2020 | Chatterjee et al. |
| 2002/0107668 | A1 | 8/2002 | Costa et al. |
| 2002/0152035 | A1 | 10/2002 | Perlin et al. |
| 2005/0277137 | A1 | 12/2005 | Lokshin et al. |
| 2006/0269111 | A1 | 11/2006 | Stoecker et al. |
| 2008/0131251 | A1 | 12/2008 | Mansfield |
| 2009/0286957 | A1 | 11/2009 | Toporik et al. |
| 2010/0088264 | A1 | 4/2010 | Teverovskiy et al. |
| 2010/0105564 | A1 | 4/2010 | Park et al. |
| 2010/0136553 | A1 | 6/2010 | Black et al. |
| 2010/0228727 | A1 | 9/2010 | Hisanaga et al. |
| 2010/0255470 | A1 | 10/2010 | Benkaitis-Davis et al. |
| 2010/0273661 | A1 | 10/2010 | Qiu et al. |
| 2011/0045481 | A1 | 2/2011 | Gladding et al. |
| 2012/0066163 | A1 | 3/2012 | Balls et al. |
| 2013/0006991 | A1 | 1/2013 | Nagano et al. |
| 2013/0238251 | A1 | 9/2013 | Zhu et al. |
| 2013/0332083 | A1* | 12/2013 | Van Laar ............... G16B 40/00 702/19 |
| 2014/0234880 | A1 | 8/2014 | Tempst et al. |
| 2015/0161516 | A1 | 6/2015 | Ghassemzadeh et al. |
| 2015/0237834 | A1 | 8/2015 | Schab et al. |
| 2016/0196758 | A1 | 7/2016 | Causevic et al. |
| 2017/0003212 | A1 | 1/2017 | Janse et al. |
| 2017/0061093 | A1* | 3/2017 | Amarasingham ...... G16H 40/63 |
| 2017/0091937 | A1 | 3/2017 | Barnes et al. |
| 2017/0189513 | A1 | 7/2017 | Mahr et al. |
| 2017/0342500 | A1 | 11/2017 | Marquard et al. |
| 2018/0285685 | A1 | 10/2018 | Singh et al. |
| 2019/0005115 | A1 | 1/2019 | Warrier et al. |
| 2019/0027252 | A1 | 1/2019 | Calhoun et al. |
| 2019/0028556 | A1 | 1/2019 | Ben-Harrush et al. |
| 2019/0050534 | A1 | 2/2019 | Apte et al. |
| 2019/0214141 | A1 | 7/2019 | Chatterjee et al. |

FOREIGN PATENT DOCUMENTS

| | | |
|---|---|---|
| CN | 107239448 | 10/2017 |
| JP | 2016537699 A | 12/2016 |

OTHER PUBLICATIONS

Joseph Gerrein, "Using Gene and microRNA Expression in the Human Airway for Lung Cancer Diagnosis," Submitted in partial fulfillment of the requirements for the degree of Doctor of Philosophy, Boston University Graduate School of Arts and Sciences and College of Engineering, 2014. (Year: 2014).*

Mell et al., "The NIST Definition of Cloud Computing", National Institute of Standards and Technology, U.S. Dept. of Commerce, NIST Special Publ. 800-145, Sep. 2011, 7 pages.

Hsiao-Lin Hwa et al., "Journal of Evaluation in Clinical Practice," Prediction of Breast Cancer and Lymph Node Metastatic Status With Tumour Markers Using Logistic Regression Model, published Dec. 12, 2006, 7 pages.

Notification of Transmittal of the International Search Report and Written Opinion, the International Search Report and the Written Opinion dated Apr. 8, 2019, for PCT Application Serial No. PCT/IB2018/060485, filed Dec. 21, 2018, 9 pages.

List of IBM Patents or Patent Applications Treated as Related, Aug. 9, 2019, 2 pages.

List of IBM Patents or Patent Applications Treated as Related, Jun. 24, 2020, 2 pages.

Jing et al., "Novel Hybrid Method for Gene Selection and Cancer Prediction", International Journal of Computer, Electrical, Automation, Control and Information Engineering vol. 4, No. 2, 2010, 8 pages.

Ma et al., "Supervise Group Lasso with applications to microarray data analysis," BMC Bioinformatics, vol. 8, No. 50. (Year: 2007).

Li et al., "High-Throughout Mammographic-Density Measurement: A Tool for Risk Prediction of Breast Cancer," BioMed Central, vol. 14, No. R114, (Year: 2012).

Vidarsson et al., "IgG Subclasses and Allotypes: From Structure to Effector Functions," Frontiers in Immunology, vol. 5, Article 520. (Year: 2014).

Examination Report—GB Application No. GB2011046.6, dated Sep. 1, 2020, 5 pages.

Notice of Reasons of Refusal of Japanese Application No. 2020-535049, dated Jun. 17, 2022, 3 Pages, English Translation.

* cited by examiner

LIBRARY SCREENING FOR CANCER PROBABILITY

BACKGROUND

In the United States, approximately one (1) in eight (8) women (i.e., twelve (12) percent) will develop invasive breast cancer over the course of a lifetime. Prior to 2017, public health organization have estimated that 252,710 new cases of invasive breast cancer would be diagnosed in women in the United States, with 63,410 new cases of non-invasive (in situ) breast cancer. In situ cases of cancer are those where malignant cells are present as a tumor, but have neither metastasized nor invaded beyond the basement membrane of where the tumor was discovered. Despite improvements in treatments, the death toll for women in the United States from breast cancer in 2017 was estimated to be about 40,610, which represents a decrease, as the toll has decreased each year from 1989, especially in women under fifty (50). However, breast cancer remains the leading cause of death from any type of cancer, among women in the United States. It is estimated that about thirty (30) percent of newly diagnosed cancers in women will be breast cancers. Although there are certain genetic indicators for increased breast cancer risks, about eight five (85) percent of breast cancers occur in women who have no family history of breast cancer. Presently, the most significant risk factors for breast cancer are gender (being a woman) and age (growing older).

SUMMARY

Shortcomings of the prior art are overcome and additional advantages are provided through the provision of a computer program product for predicting likelihood of a condition. The computer program product comprises a storage medium readable by a processing circuit and storing instructions for execution by the processing circuit for performing a method. The method includes, for instance: obtaining, by the one or more processors, a raw data set comprising peptide libraries of patients designated as either diagnosed or pre-diagnosed with a condition or not diagnosed with the condition; segmenting, by the one or more processors, the raw data set into a pre-defined number of groups, wherein the segmenting comprises separating out a holdout group of data from the remaining groups; performing, by the one or more processors, a principal component analysis on the remaining groups to identify, based on a frequency of features in the remaining groups, by the one or more processors, common features in data of the remaining groups and weighting the common features based on frequency of occurrence in the remaining groups, wherein the common features comprise principal components represented by coefficients; determining, by the one or more programs, a smallest number of the principal components that yields a pre-defined level of validation accuracy; and generating, by the one or more processors, a predictive model, by utilizing the smallest number of principal components as parameters for a best fit in a logistic regression model, wherein the predictive model provides binary outcomes selected from the group consisting of: likelihood of presence of the condition within a pre-defined threshold or no likelihood of the presence of the condition within the pre-defined threshold.

Shortcomings of the prior art are overcome and additional advantages are provided through the provision of a method of predicting likelihood of a condition. The method includes, for instance: obtaining, by one or more processors, a raw data set comprising peptide libraries of patients designated as either diagnosed or pre-diagnosed with a condition or not diagnosed with the condition; segmenting, by the one or more processors, the raw data set into a pre-defined number of groups, wherein the segmenting comprises separating out a holdout group of data from the remaining groups; performing, by the one or more processors, a principal component analysis on the remaining groups to identify, based on a frequency of features in the remaining groups, by the one or more processors, common features in data of the remaining groups and weighting the common features based on frequency of occurrence in the remaining groups, wherein the common features comprise principal components represented by coefficients; determining, by the one or more programs, a smallest number of the principal components that yields a pre-defined level of validation accuracy; and generating, by the one or more processors, a predictive model, by utilizing the smallest number of principal components as parameters for a best fit in a logistic regression model, wherein the predictive model provides binary outcomes selected from the group consisting of: likelihood of presence of the condition within a pre-defined threshold or no likelihood of the presence of the condition within the pre-defined threshold.

Shortcomings of the prior art are overcome and additional advantages are provided through the provision of a system for predicting likelihood of a condition. The system includes a memory, one or more processor in communication with the memory, and program instructions executable by the one or more processor via the memory to perform a method. The method includes, for instance: obtaining, by the one or more processors, a raw data set comprising peptide libraries of patients designated as either diagnosed or pre-diagnosed with a condition or not diagnosed with the condition; segmenting, by the one or more processors, the raw data set into a pre-defined number of groups, wherein the segmenting comprises separating out a holdout group of data from the remaining groups; performing, by the one or more processors, a principal component analysis on the remaining groups to identify, based on a frequency of features in the remaining groups, by the one or more processors, common features in data of the remaining groups and weighting the common features based on frequency of occurrence in the remaining groups, wherein the common features comprise principal components represented by coefficients; determining, by the one or more programs, a smallest number of the principal components that yields a pre-defined level of validation accuracy; and generating, by the one or more processors, a predictive model, by utilizing the smallest number of principal components as parameters for a best fit in a logistic regression model, wherein the predictive model provides binary outcomes selected from the group consisting of: likelihood of presence of the condition within a pre-defined threshold or no likelihood of the presence of the condition within the pre-defined threshold.

Methods and systems relating to one or more aspects are also described and claimed herein. Further, services relating to one or more aspects are also described and may be claimed herein.

Additional features and advantages are realized through the techniques described herein. In some embodiments of the present invention, the method includes testing, by the one or more processors, the predictive model, by applying the coefficients to calculate features to use for the holdout group; and tuning, by the one or more processors, the predictive model by comparing the features for the holdout group to the principal components. In some embodiments of the present invention, the peptide libraries comprise 12-mer peptide libraries and/or the condition comprises Stage I breast cancer. In some embodiments of the present invention, segmenting comprises generating random numbers to select which record of the raw data set to assign to which of the groups.

In some embodiments of the present invention, the method includes, prior to performing the principal component analysis, normalizing, by the one or more processors, the peptides comprising the raw data set by adding peptide values of the peptides across all the peptides and dividing each expression value by a resultant sum to compute a ratio.

In some embodiments of the present invention, performing a principal component analysis on the remaining groups comprises: generating, by the one or more processors, sets of training data, wherein each set of training data of the sets of training data comprises data in all but one group of the remaining groups; performing, by the one or more processors, a principal component analysis individually on each set of training data to identify common features in each set of training data; executing, by the one or more programs, a principal component analysis utilizing the remaining groups as a single training set to identify common features in the single training set; and performing a cross-validation of the common features of each set of training data and the common features in the single training set, wherein the cross-validation is of a number of folds equal to a number of the remaining groups, to identify the principal components and determine the coefficients. In some embodiments of the present invention, a pre-defined level of validation accuracy is a highest validation accuracy based on the number of folds.

In some embodiments of the present invention, the method includes: obtaining, by the one or more processors, new raw data comprising a 12-mer peptide library of a given individual; and applying, by the one or more processors, the predictive model to the new raw data to determine a binary outcome for the given individual. In some embodiments of the present invention, applying the predictive model comprises performing a principal component analysis on the new raw data utilizing the coefficients and performing a logistic regression to generate the binary outcome.

BRIEF DESCRIPTION OF THE SEVERAL VIEWS OF THE DRAWINGS

One or more aspects are particularly pointed out and distinctly claimed as examples in the claims at the conclusion of the specification. The foregoing and other objects, features, and advantages are apparent from the following detailed description taken in conjunction with the accompanying drawings in which:

DETAILED DESCRIPTION

Figure 1:
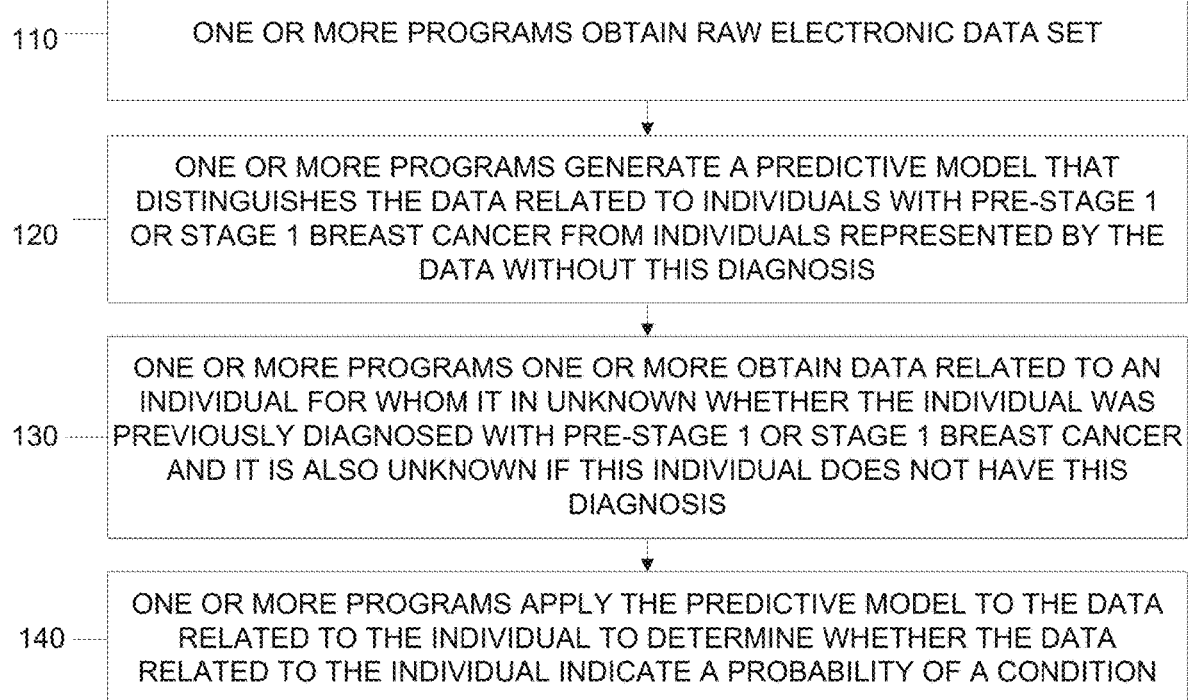
FIG. 1 depicts a workflow illustrating certain aspects of some embodiments of the present invention.

The accompanying figures, in which like reference numerals refer to identical or functionally similar elements throughout the separate views and which are incorporated in and form a part of the specification, further illustrate the present invention and, together with the detailed description of the invention, serve to explain the principles of the present invention. As understood by one of skill in the art, the accompanying figures are provided for ease of understanding and illustrate aspects of certain embodiments of the present invention. The invention is not limited to the embodiments depicted in the figures.

Figure 5:
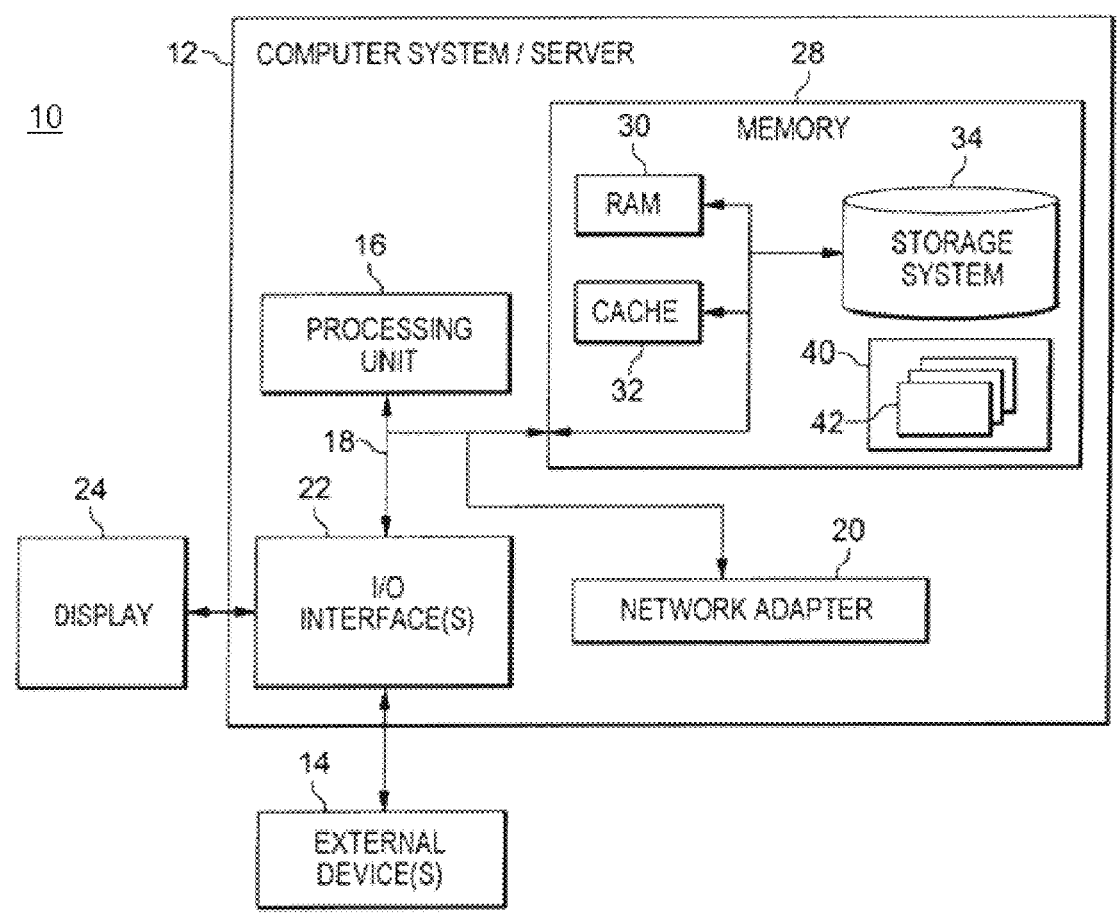
FIG. 5 depicts one embodiment of a computing node that can be utilized in a cloud computing environment.

As understood by one of skill in the art, program code, as referred to throughout this application, includes both software and hardware. For example, program code in certain embodiments of the present invention includes fixed function hardware, while other embodiments utilized a software-based implementation of the functionality described. Certain embodiments combine both types of program code. One example of program code, also referred to as one or more programs, is depicted in FIG. 5 as program/utility 40, having a set (at least one) of program modules 42, may be stored in memory 28.

Embodiments of the present invention include a computer-implemented method, a computer program product, and a computer system that recognize an increased probability of an eventual presence of breast cancer where one or more programs apply a twelve (12) amino acid (12-mer) peptide library, Immunoglobulin G (IgG) antibody, and various computerized data modeling and computerized management to make this determination within an acceptable level of accuracy. A peptide library is comprised of random deoxyribonucleic acid (DNA) sequences that encode various peptides, which can recognize a target fused on the bacteriophages. Meanwhile IgG is the most abundant type of antibody, found in all body fluids and protects against bacterial and viral infections.

Aspects of embodiments of the present invention represent improvements to existing computing technology and are inextricably tied to computing. Specifically, embodiments of the present invention represent improved methods of handling large volumes of data and for building logistical models from the data. For example, embodiments of the present invention reduce the observed data rate in the eventual results because the program code preprocesses the data utilized to build a pattern, rather than using a less efficient binary binning procedure.

Aspects of embodiments of the present invention are inextricably tied to computing at least because the electronic models, including automatically generated self-learning predictive models generated from training data, generated by embodiments of the present invention cannot be generated outside of computing and do not exist outside of computing. Records initially utilized in embodiments of the present invention are electronic records in one or more data set, contained in one or more database, that are machine readable. The resultant models are also electronic and are applied to additional electronic data sets utilizing computing resources. Because of both the volume and the nature of data, an individual is not capable of accomplishing the specific aspects of embodiments of the present invention that result in a machine readable data model that can be applied by program code to additional data sets in order to identify records with a probability of an event or condition that the model was generated to predict the probable presence of breast cancer at a (e.g., pre-defined) time in the future.

Embodiments of the present invention provide utility that individuals and existing systems are incapable of because of the speed at which they are able to provide results. To be useful, program code in embodiments of the present invention both generates and updates models and provides results (identification of records that comport with the model), within a limited temporal period. For example, in a scenario where an individual visits a healthcare provider, the individual and the provider would benefit from acquiring information regarding whether the individual, as represented electronically with isolated values in a data (peptide) library, has items in the record that match the data sought by predictive model. If this information cannot be provided within the visit, it is arguably not useful to the individual or the healthcare provider. Thus, in embodiments of the present invention, the program code analyzes a given sample of an individual and applies the predictive model in real-time, or close to real-time. Thus, embodiments of the present invention enable real-time analysis of an electronic data library, based on whether the large volume of peptides chronicled in the library comport with a predictive model generated by program code in embodiments of the present invention.

Embodiments of the present invention provide advantages and improvements that are inextricably tied to computer technology also because embodiments of the present invention offer certain advantages that increase computational efficiency and efficacy. For example, as described in greater detail later on, embodiments of the present invention utilize distributed processing based on anticipated query results in order to decrease the timeline for key analytic deliverables. This distributed processing enables the program code to perform multiple analysis processes simultaneously. Portions of certain embodiments of the present invention can be migrated to a cloud architecture and made available to users as software as a service (SaaS) offerings. The unlimited computational capacity of resources in a cloud architecture are suited to support the program code's distribution of simultaneous queries and processes in order to meet the efficiency demands of the system in a data rich environment.

Embodiments of the present invention also provide advantages and improvements that are inextricably tied to computer technology because they utilize machine learning. One advantageous aspect of some embodiments of the present invention over existing approaches to event (e.g., condition) identification in data dense environments is that some other methods approach the problem of event identification and recognition as a statistical problem, instead of a machine learning one, which is an approach that limits the options in available tools. By utilizing machine learning, embodiments of the present invention can identify records that include an event where the information directly identifying the event is absent. For example, by using machine learning, program code can identify an individual patient with a probability of developing breast cancer using a 12-mer peptide library of an undiagnosed patient, i.e., where the data does not already indicate that the disease is present in the patient. In some cases, the program code can utilize machine learning to indicate that an individual has a threshold probability of developing breast cancer when the opposite is indicated in data related to that individual. Thus, the program code is not merely identifying and retrieving existing established data stored in one or more memory device. Rather, the program code establishes a pattern, continuously trains a machine learning algorithm to apply the pattern, and utilizes the resultant predictive model to identify instances of an event not already explicitly indicated by the data.

In an embodiment of the present invention, one or more programs exploit principal component analysis (PCA), which is a statistical procedure, to determine a related set of concepts or components to one or more features matching a number of individuals in a training set of data. PCA comprises an orthogonal transformation to convert a set of observations of possibly correlated variables into a set of values of linearly uncorrelated variables called principal components. The number of principal components is less than or equal to the number of original variables. Thus, in an embodiment of the present invention, the program code exploits a parent concept to generate multiple sub-components. This transformation is defined in such a way that the first principal component has the largest possible variance (that is, accounts for as much of the variability in the data as possible), and each succeeding component in turn has the highest variance possible under the constraint that it is orthogonal to the preceding components. The resulting vectors are an uncorrelated orthogonal basis set. PCA is sensitive to the relative scaling of the original variables.

Aspects of various embodiments of the present invention provide advantages over existing systems of utilizing computer-implemented method, computing systems, and/or computer program products to predict probabilities of breast cancer in individuals, based on generating and applying a predictive model. Existing methods have relied on breast cancer markers on polymorphisms, changes in the genetic code of DNA, taking tissue, urine and/or milk samples to detect overexpressed biomarkers, utilizing mass spectrometry to analyze pre-operative samples, analyzing gene expression profiles, analyzing gene expression data from ribonucleic acid (RNA), and introducing immunotherapeutic agents or vaccines to trigger responses. In contrast to these existing methods, in embodiments of the present invention, one or more programs generate and apply a predictive model based, in part, on analyzing immunosignature samples of 12-mer peptides and training the program code to both generate and recognize patterns indicative of a quantifiable risk in a patient of breast cancer.

Figure 2:
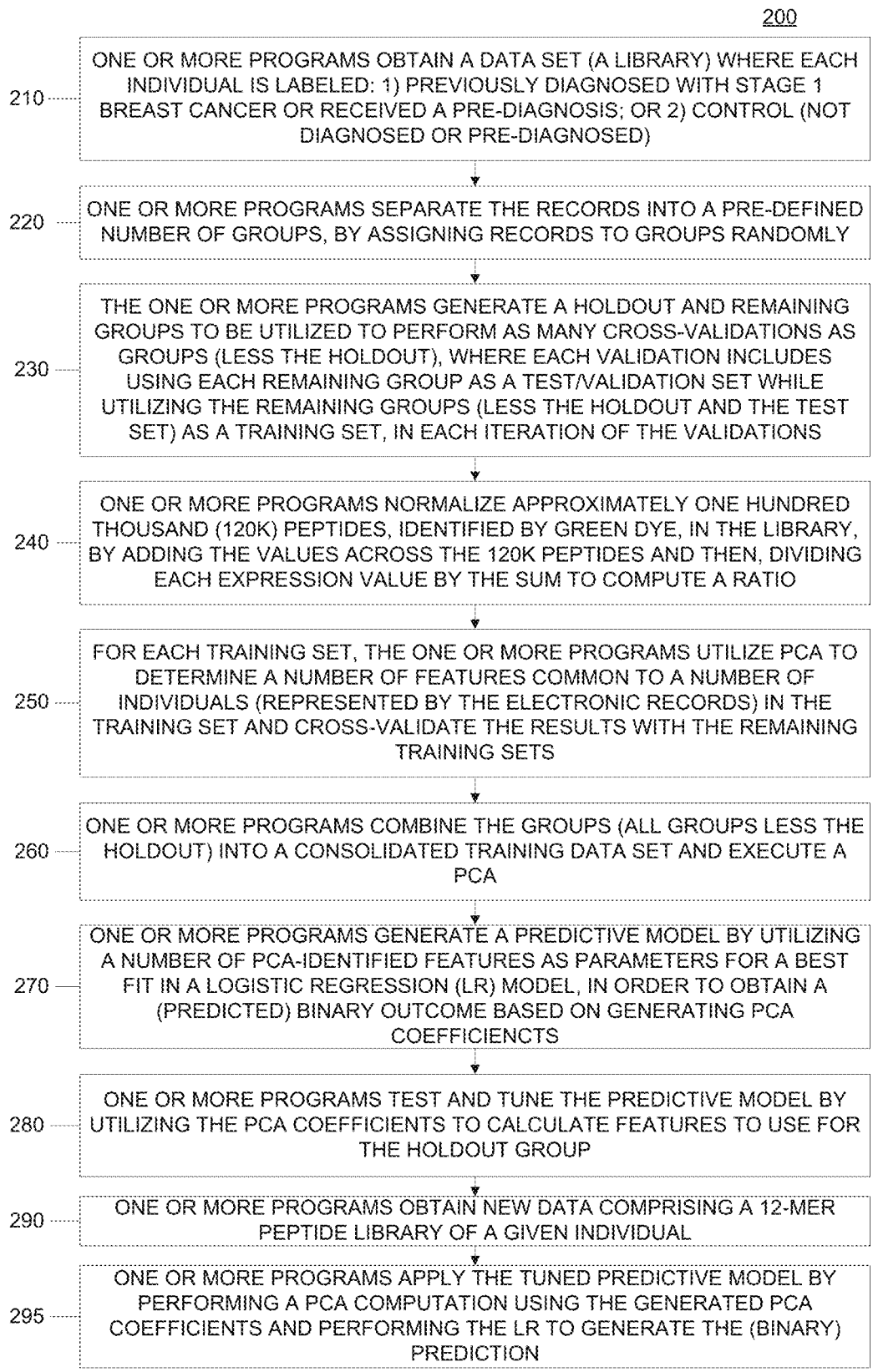
FIG. 2 depicts a workflow illustrating certain aspects of some embodiments of the present invention.

FIG. 1 provides a general workflow 100 of some aspects of certain embodiments of the present invention. FIG. 2 is a workflow 200 that further details aspects included in the workflow 100 of FIG. 1.

Referring first to FIG. 1, in some embodiments of the present invention, one or more programs obtain raw electronic data set (110). In an embodiment of the present invention, the raw electronic data comprises raw data from a 12-mer peptide library screening using anti-human IgG antibody. The data set may include up to one hundred twenty thousand (120K) values, where each value represents a twelve (12) amino acid long peptide isolated by a method, including but not limited to fluorescent labeling, including the use of a green dye. The data set includes data pertaining to individuals who were previously diagnosed with pre-Stage I or Stage I breast cancer and individuals who do not have this diagnosis. The records in the data set are labeled to indicate this characterization.

Utilizing the data set, the one or more programs generate a predictive model that distinguishes the data related to individuals with pre-Stage I or Stage I breast cancer from individuals represented by the data without this diagnosis (120). The predictive model generated by the one or more programs in embodiments of the present invention can be understood as a classifier or a classifier algorithm. The process for generating the predictive model is discussed in greater detail in FIG. 2. However, the one or more programs, in generating the predictive model, utilize the data set as training data, and generate, based on the training provided by this data set, the predictive model.

The one or more programs obtain data related to an individual for whom it in unknown whether the individual was previously diagnosed with pre-Stage I or Stage I breast cancer and it is also unknown if this individual does not have this diagnosis (130). In an embodiment of the present invention, the data comprises values for respective peptides in the 12-mer library for this individual. The data may comprise 120K values.

In an embodiment of the present invention, the one or more programs apply the predictive model to the data related to the individual to determine whether the data related to the individual indicate a probability of a condition (140). The condition may be one or more of a likelihood (within a given range) that the individual will be diagnosed with breast cancer (e.g., for an individual with a tumor) and/or a likelihood that the individual will be diagnosed with breast cancer within a given time period from the application of the predictive model. For example, some embodiments of the present invention generate models that return a probability of a condition being identified at a future time, including but not limited to, two (2) years after the one or more programs apply the model.

FIG. 2 is a more detailed workflow 200, when compared to FIG. 1, which illustrates various aspects of some embodiments of the present invention. As illustrated in FIG. 1, in some embodiments of the present invention, the one or more programs obtain raw electronic data (110) and utilize this data to generate a predictive model (120). FIG. 2 provides additional details regarding the generation of this model.

Referring to FIG. 2, in an embodiment of the present invention, the one or more programs obtain a data set where each individual record is labeled in accordance with belonging to one of two categories: 1) being related to an individual who was previously diagnosed with either Stage I breast cancer or received a pre-diagnosis of this cancer; or 2) being related to an individual who was expressly not diagnosed with this cancer (i.e., utilizing traditional means of diagnosis, there are no indications that the individual has or has the beginning stages of this cancer) (210). As will be discussed later, the data includes identification of 12-mer peptides and can be understood as peptide libraries. In embodiments of the present invention, the one or more programs process data in order to improve the efficiency of the model generation. In some embodiments of the present invention, the one or more programs separate the data into an amino acid sequence part (e.g., dim: 1100+ by 120 k+) and feature part (e.g., dim: 1100+ by 5, including sample id, status, source, preDx, and wafer).

The one or more programs separate the records into a pre-defined number of groups, by assigning records to groups randomly (220). In some embodiments of the present invention, the one or more programs generate multiple random seeds and for each seed, separate the records into the pre-defined number of groups. For example, if a random number is twenty-five (25), the one or more programs will assign each $25^{th}$ record to one of the groups. The one or more programs will continually generate various seeds and utilize these seeds to make the random assignments of the records to the groups. The groups are generated by the one or more programs such as each group contains an equal (or similar) amount of data as each other group. In an embodiment of the present invention, based on the randomization, the one or more programs separate the records into six (6) groups.

In embodiments of the present invention when the one or more programs assign the data to six (6) groups of data sets (e.g., 2K-mer by 3 channels), both parts, the amino sequence part and the feature part may be stored as a list object in R with a number of sub-lists equal to the number of groups (e.g., 6), the names of which follows the file name. Sample-id-and-label pairs may be shared by all sub data sets to form a table. Sample id and status (or label) are combined as key to index the amino acid sequence data. To filter classes or sample ids, etc., the one or more programs can perform the filtering in this small table and then use the row index to extract corresponding amino acid sequence data. When the one or more programs filter the amino acid sequence data (to keep samples shared by all data sets), the one or more programs change the row order to be the same order as that in the table. In embodiments of the present invention, to handle imbalanced classes, the one or more programs utilize down and up sampling to create balanced distribution of the classes for training The one or more programs select one (1) group of the groups the one or more programs generated as a holdout and designate the remaining groups for performing as many cross-validations as groups (less the holdout), where each validation includes using each remaining group as a test/validation set while utilizing the remaining groups (i.e., less the holdout and the test set) as a training set, in each iteration of the validations (230). As part of a PCA analysis (e.g., 250), which will be discussed herein, the one or more programs perform this validation as many times (i.e., folds) as there are a number of groups (less the separated group). Thus, if the one or more programs generated six (6) groups, the one or more programs perform a five (5) fold cross-validation. In performing this validation, of the groups that are involved in the cross-validation (i.e., the total number of groups less the group deducted initially), another one (1) group is pulled out as a test group. The one or more programs utilize the remaining groups (i.e., all groups less the initially subtracted group and the test group) for training, while the test group is utilized to perform a validation. The one or more programs repeat this operation a number of times equal to the number of groups (less the first subtracted group), in a circular manner, such that each group of these groups is utilized by the one or more programs as a validation set. Thus, the number of folds in the cross-validation is equivalent to the number of training sets of data.

Returning to the example of six (6) groups. With six (6) groups, the one or more programs separate out a first group. The one or more programs utilize the five (5) remaining groups to perform a 5-fold cross-validation. In performing this validation, the one or more programs select a group of the five (5) groups as a test group and perform a validation with that group, while utilizing the remaining groups as training data. The one or more programs repeat this validation step, varying which of the five (5) groups is designated as the test group. The one or more programs repeat this operation in a cyclical manner until all each of the five (5) groups serves as the test group.

Returning to FIG. 2, in some embodiments of the present invention, for each sample (or individual, as represented by the electronic records), the one or more programs normalize approximately one hundred thousand (120K) peptides, identified by green dye, in the library, by adding the values across the 120K peptides and then, dividing each expression value by the sum to compute a ratio (240). Normalizing the values enables the one or more programs to compare expression values across individuals and 120K peptide library. In an embodiment of the present invention, to normalize, the one or more programs add expressions across the 120K peptides for each individual's sample and then the respective expressions are divided by the sum.

The 120K number is used as an example in the embodiments illustrated in FIG. 2, but as understood by one of skill in the art, more or less peptides can be identified in various samples and utilized in embodiments of the present invention.

In some embodiments of the present invention, for each training set (as designated above when a test group is excluded by the groups, less the first hold out group), one or more programs utilize PCA to determine a number of features common to a number of individuals (represented by the electronic records) in the training set (250). The PCA analysis provides stable values across the cross-validation steps for each random number seed used. As understood by one of skill in the art, PCA comprises an orthogonal transformation to convert a set of observations of possibly correlated variables into a set of values of linearly uncorrelated variables called principal components. The number of principal components is less than or equal to the number of original variables. Thus, in an embodiment of the present invention, the program code exploits identified expression values (through the normalization), to generate multiple common features, based on the test data. This transformation is defined in such a way that the first principal component has the largest possible variance (that is, accounts for as much of the variability in the data as possible), and each succeeding component in turn has the highest variance possible under the constraint that it is orthogonal to the preceding components. The resulting vectors are an uncorrelated orthogonal basis set. PCA is sensitive to the relative scaling of the original variables.

Returning to FIG. 2, in an embodiment of the present invention, the one or more programs execute a PCA to determine features that are relevant to individuals represented in the test data (e.g., 250). In the PCA, the one or more programs determine which features are most representative in the test data. In part as a results of the PCA, the eventual model generated by the one or more programs may include a cumulative understanding of the features common to the individuals. The one or more programs utilize this data to infer which features have the highest variance and the one or more programs may determine an order for the terms.

The one or more programs run the PCA (e.g., 250) inside the cross validation. For every step of cross validation, the one or more programs run PCA on the training set and transform the validation using the loadings from this PCA result, before feeding them into the model for prediction, to compute validation accuracy. In an embodiment of the present invention, the one or more programs perform a PCA on each training set, per cross validation step, as well as the final evaluation step (e.g., 260, discussed later), and write the list of results to a file for each sub data set. The one or more programs read this PCA result file will be read into memory when its contents are utilized in cross validation and modeling.

Figure 3:
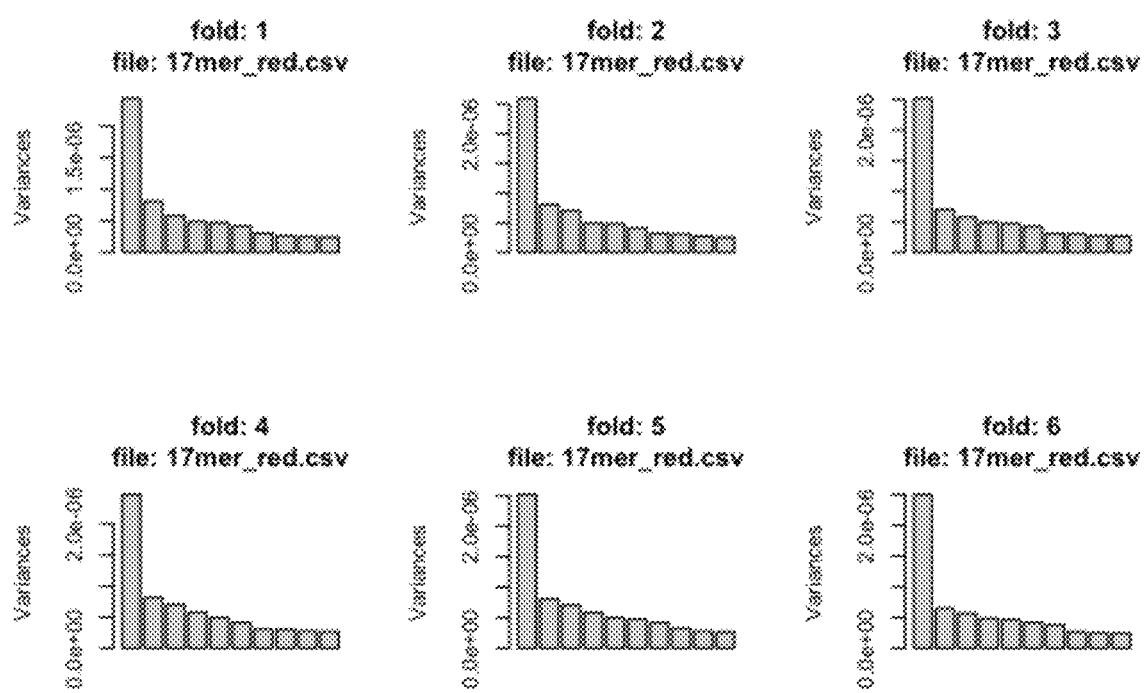
FIG. 3 depicts certain aspects of an embodiment of the present invention.

After completing the PCA of the individual test data groups, the one or more programs combine the groups (e.g., the five (5) groups in the 5-fold example, all groups less the holdout) into a consolidated training data set and execute a PCA (260). FIG. 3 is an example of PCA results obtained by the one or more programs on training sets, wherein the folds 1-5 are results on individuals training sets and fold 6 is a result on the whole cross-validation.

The one or more programs generate a predictive model by utilizing a number features identified through PCA (e.g., selected based on dominance) as a parameters for a best fit in a Logistic Regression (LR) model, in order to obtain a (predicted) binary outcome (e.g., Stage I breast cancer within a degree of error or control data, like the original labeled data) (270). A result of this aspect is the generation of PCA coefficients (e.g., 270). As illustrated in FIG. 2, in some embodiments of the present invention, the one or more programs apply a PCA to the data set and utilize the resultant principal components to build a logistic regression model, with the aim to predict (binary) class labels, in this case, Stage I or control. As demonstrated in FIGS. 2-3, the one or more programs utilize cross validation to tune the best number of principal components to be included in the model (e.g., 10 means the first 10 components, 100 means the first 100 components). The one or more programs select the smallest (best) number that yields the highest validation for the number of folds. For example, in embodiments of the present invention that utilize a total of six groups and 5-fold validation, the one or more programs select the smallest (best) number that yields the highest 5-fold validation accuracy. The one or more programs evaluate the accuracy of the test based on a model using this parameter. In these 6-group embodiments of the present invention, the one or more programs perform the cross-validation and determine that an LR model with several principal components from 12-mer (green) yields an average validation accuracy up to 95%, and that high accuracy holds on evaluation on the test set.

In some embodiments of the present invention, the one or more programs utilize a single PCA-derived feature to generate the model (e.g., utilizing the most dominant feature that explains the variance in the data). For example, some models may only include the first three derived principal components from the 12-mer data as they may yield an average validation accuracy of 95.08% 0.005% and average validation area under the ROC curve (AUC) of 96.02% 0.006%, and test accuracy of 96.72% and test AUC of 95.55%. In some embodiments of the present invention, the one or more programs select a parameter that yields a highest validation accuracy and validation AUC.

The one or more programs test and tune the predictive model (a best fit model) by utilizing the PCA coefficients to calculate features to use for the hold out data (the group that was originally held out) (280). This tuning, as well as the repetitive PCA procedures described, can be understood as machine learning—by repeating various steps utilizing a data set with known information, the one or more programs can tune and improve the accuracy of the recognized features (patterns) that the model will utilize to determine whether a condition is present.

The one or more programs obtain a new sample of data comprising a 12-mer peptide library of a given individual (290). The one or more programs score the individual for predicting the outcome of the presence or absence of potential Stage I breast cancer with a probability by applying the tuned predictive model (295). The one or more programs apply the tuned predictive model by performing a PCA computation using the generated PCA coefficients and performing the LR to generate the (binary) prediction (e.g., probability of Stage I or no obtainable probability of Stage I, based on the model). Thus, the one or more programs utilize the principal components as a tuning parameter for the predictive model.

Figure 4:
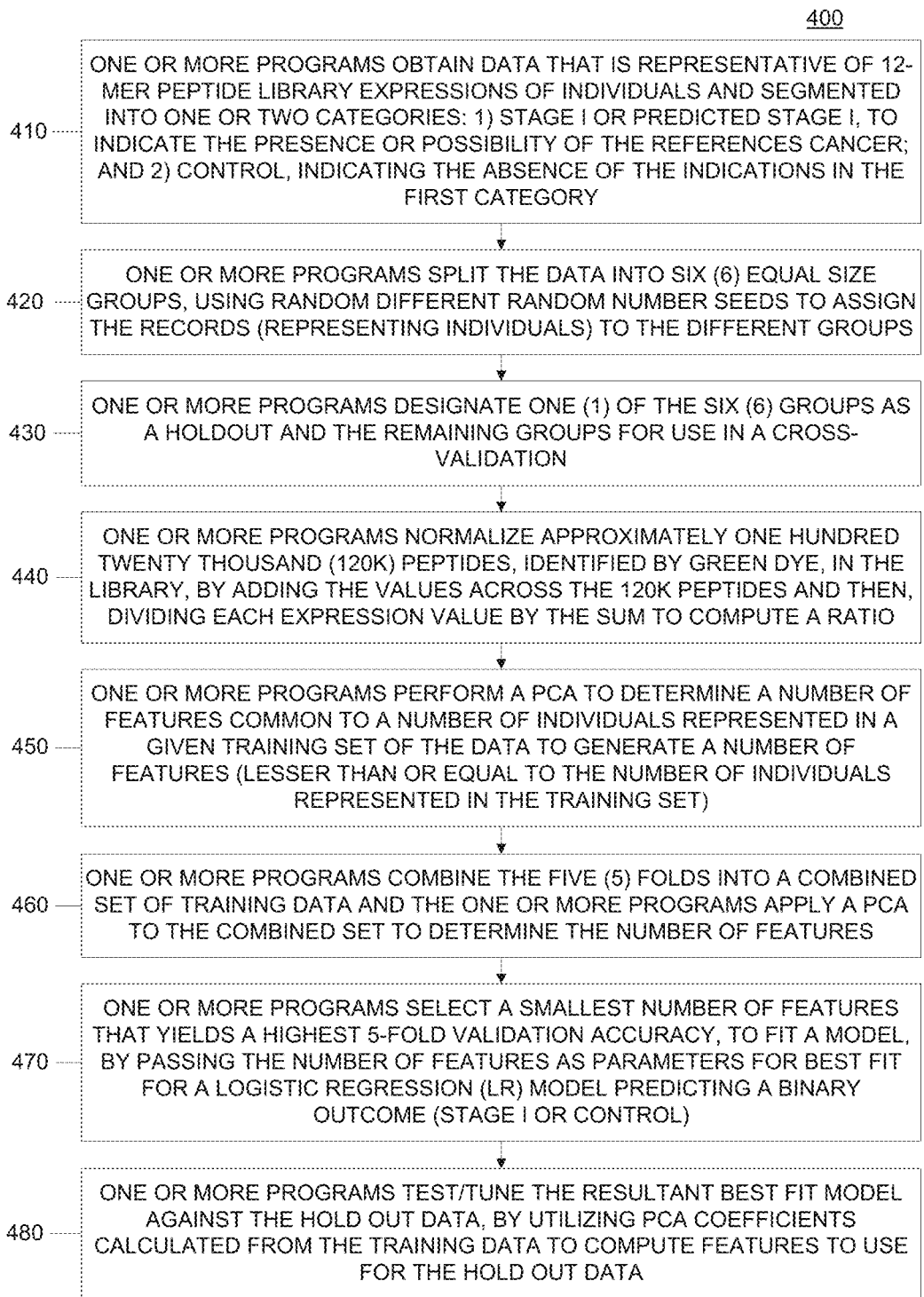
FIG. 4 depicts a workflow illustrating certain aspects of some embodiments of the present invention.

FIG. 4 is a workflow 400 that illustrates certain aspects of some embodiments of the present invention. Specifically, the one or more programs illustrate an embodiments where the one or more programs divide obtained data into six (6) groups. In some embodiments of the present invention, one or more programs obtain data that is representative of 12-mer peptide library expressions of individuals and segmented into one or two categories: 1) Stage I or predicted Stage I, to indicate the presence or possibility of the references cancer; and 2) control, indicating the absence of the indications in the first category (410). The one or more programs split the data into six (6) equal size groups, using random different random number seeds to assign the records (representing individuals) to the different groups (420).

The one or more programs designate one (1) of the six (6) groups as a holdout and the remaining groups for use in a cross-validation (430). As discussed above, the validation is a 5-fold cross validation, as the one or more programs repeat the validation five times, in a circular fashion, until every group is used as a validation set. The one or more programs normalize the expression values for approximately 120K peptides in a library by adding up the values across the 120K peptides and then dividing each expression value by the sum to compute a ratio (440). In an embodiment of the present invention, to normalize, the one or more programs add expressions across the 120K peptides for each individual's sample and then the respective expressions are divided by the sum. The one or more programs perform a PCA to determine a number of features common to a number of individuals represented in a given training set of the data to generate a number of features (lesser than or equal to the number of individuals represented in the training set) (450). There are four (4) training sets of the data and each training set consists of four (4) of the five (5) groups that are not the holdout group. The one or more programs performs PCA on each training set.

The one or more programs combine the five (5) folds into a combined set of training data and the one or more programs apply a PCA to the combined set to determine the number of features (460). As the one or more programs run PCA within cross-validations, in all, the one or more programs perform a PCA for 6 sub data sets*(5 folds+1 cv set as a whole for test)=thirty six (36) times. The one or more programs select a smallest number of features that yields a highest 5-fold validation accuracy, to fit a model, by passing the number of features as parameters for best fit for a Logistic Regression (LR) model predicting a binary outcome (Stage I or control) (470). The one or more programs test/tune the resultant best fit model against the hold out data, by utilizing PCA coefficients calculated from the training data to compute features to use for the hold out data (480).

Once the model is created, any new sample of 12-mer peptide library expression for an individual can be scored using that model for predicting the outcome of an absence or presence of potential Stage I breast cancer, with a probability. To compute the scoring on the new sample, the one or more programs perform a PCA computation using the coefficients from the training data (again) and then applying to the LR model for the prediction.

Embodiments of the present invention include a computer-implemented method, a computer program product, and a computer system, that include one or more programs executed by one or more processors obtaining a raw data set comprising peptide libraries of patients designated as either diagnosed or pre-diagnosed with a condition or not diagnosed with the condition. The one or more programs segment the raw data set into a pre-defined number of groups, wherein the segmenting comprises separating out a holdout group of data from the remaining groups. The one or more programs perform a principal component analysis on the remaining groups to identify, based on a frequency of features in the remaining groups, by the one or more processors, common features in data of the remaining groups and weighting the common features based on frequency of occurrence in the remaining groups, where the common features comprise principal components represented by coefficients. The one or more programs determine a smallest number of the principal components that yields a pre-defined level of validation accuracy. The one or more programs generate a predictive model, by utilizing the smallest number of principal components as parameters for a best fit in a logistic regression model, wherein the predictive model provides binary outcomes selected from the group consisting of: likelihood of presence of the condition within a pre-defined threshold or no likelihood of the presence of the condition within the pre-defined threshold.

In some embodiments of the present invention, the one or more programs also test the predictive model, by applying the coefficients to calculate features to use for the holdout group; and tune the predictive model by comparing the features for the holdout group to the principal components. The peptide libraries may comprise 12-mer peptide libraries. The condition may comprise Stage I breast cancer.

In some embodiments of the present invention, when the one or more programs segment, the one or more programs generate random numbers to select which record of the raw data set to assign to which of the groups.

In some embodiments of the present invention, prior to performing the principal component analysis, the one or more programs normalize the peptides comprising the raw data set by adding peptide values of the peptides across all the peptides and dividing each expression value by a resultant sum to compute a ratio.

In some embodiments of the present invention, when the one or more programs perform a principal component analysis on the remaining groups, the one or more programs generate sets of training data, where each set of training data of the sets of training data comprises data in all but one group of the remaining groups. The one or more programs perform a principal component analysis individually on each set of training data to identify common features in each set of training data. The one or more programs execute a principal component analysis utilizing the remaining groups as a single training set to identify common features in the single training set; and the one or more programs perform a cross-validation of the common features of each set of training data and the common features in the single training set, where the cross-validation is of a number of folds equal to a number of the remaining groups, to identify the principal components and determine the coefficients.

In some embodiments of the present invention, a pre-defined level of validation accuracy is a highest validation accuracy based on the number of folds.

In some embodiments of the present invention, the one or more programs obtain new raw data comprising a 12-mer peptide library of a given individual. The one or more programs apply the predictive model to the new raw data to determine a binary outcome for the given individual. In some embodiments of the present invention, when the one or more programs apply the predictive model, the one or more programs perform a principal component analysis on the new raw data utilizing the coefficients and performing a logistic regression to generate the binary outcome.

Referring now to FIG. 5, a schematic of an example of a computing node, which can be a cloud computing node 10. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove. In an embodiment of the present invention, the computing resource(s) that include processing devices that executed the PCA, for example, can be understood as part of one or more cloud computing nodes 10 (FIG. 5) and if not examples of portions of a cloud computing node 10, then a portion of one or more general computing nodes that include aspects of the cloud computing node 10.

In cloud computing node 10 there is a computer system/ server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 12 that can be utilized as cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/ non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs). Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter). Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
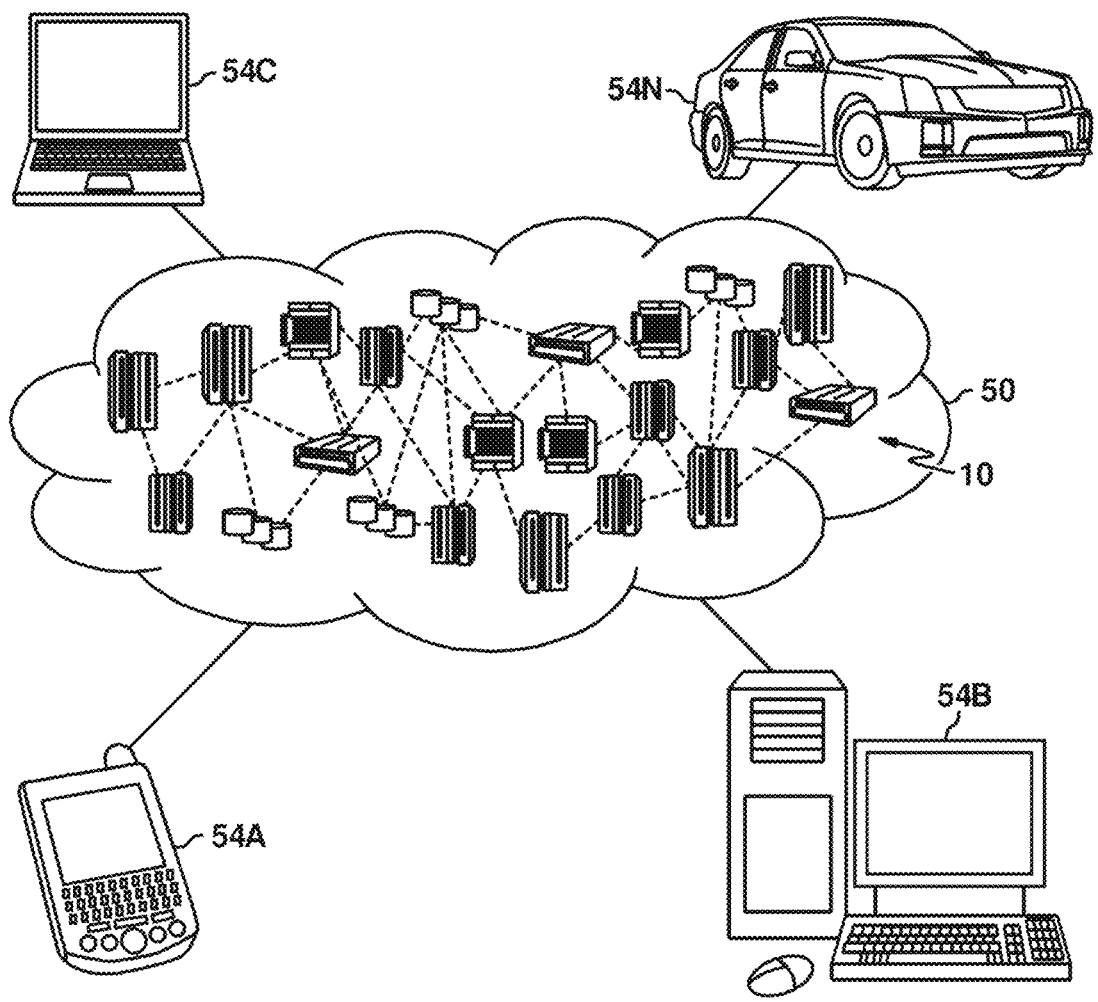
FIG. 6 depicts a cloud computing environment according to embodiments of the present invention.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 7:
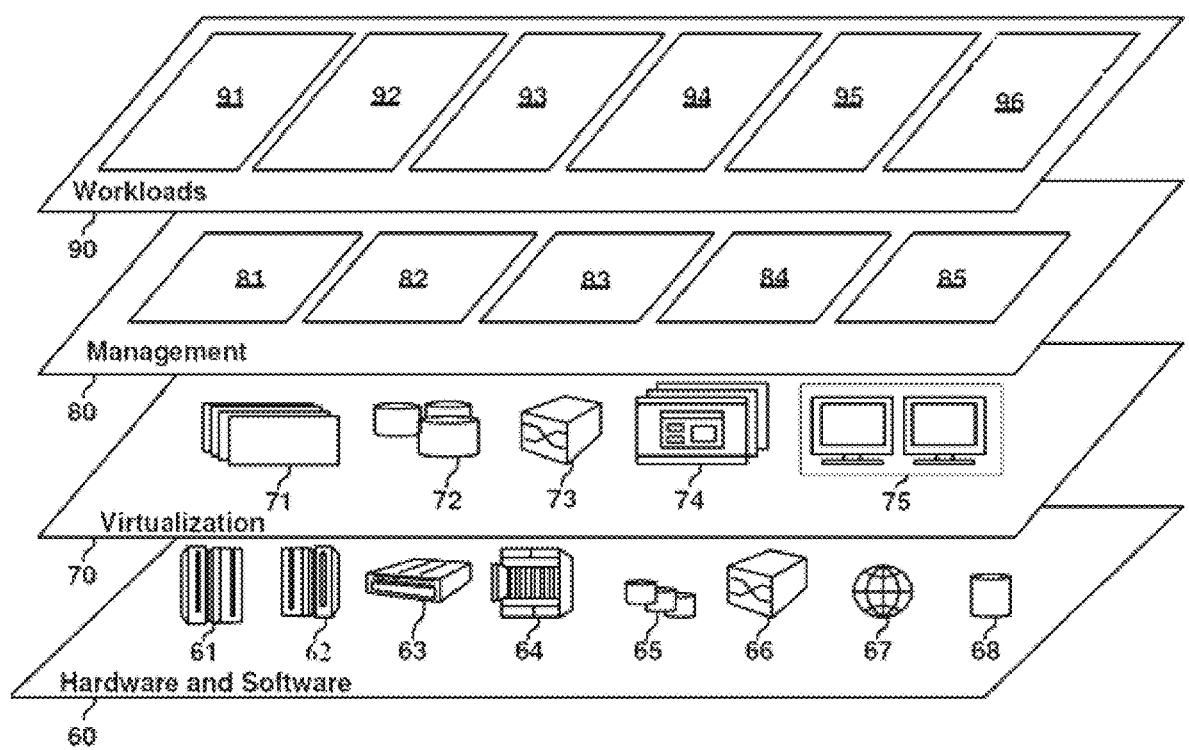
FIG. 7 depicts abstraction model layers according to embodiments of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and generating a predictive model 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A computer-implemented method comprising:
   obtaining, by the one or more processors, a raw data set comprising peptide libraries of patients designated as either diagnosed or pre-diagnosed with a condition or not diagnosed with the condition;
   segmenting, by the one or more processors, the raw data set into a pre-defined number of groups, wherein the segmenting comprises separating out a holdout group of data from data of the remaining groups;
   performing, by the one or more processors, a principal component analysis on the data of the remaining groups to identify, based on a frequency of features in the data of the remaining groups, by the one or more processors, common features in the data of the remaining groups and weighting the common features in the data of the remaining groups based on frequency of occurrence in the data of the remaining groups, wherein the common features in the data of the remaining groups comprise principal components represented by coefficients, wherein the performing the principal component analysis on the data of the remaining groups comprises:
      generating, by the one or more processors, sets of training data, wherein each set of training data of the sets of training data comprises data in all but one group of the remaining groups;
      performing, by the one or more processors, a principal component analysis individually on each set of training data to identify common features in each set of training data;
      executing, by the one or more programs, a principal component analysis utilizing the remaining groups as a single training set to identify common features in the single training set; and
      performing a cross-validation of the common features of each set of training data and the common features in the single training set to identify the principal components and determine the coefficients;
   determining, by the one or more processors, a smallest number of the principal components that yields a pre-defined level of validation accuracy;
   generating, by the one or more processors, a predictive model, by utilizing the smallest number of principal components as parameters for a best fit in a logistic regression model, wherein the predictive model provides binary outcomes selected from the group consisting of: likelihood of presence of the condition within a pre-defined threshold or no likelihood of the presence of the condition within the pre-defined threshold;
   testing, by the one or more processors, the predictive model, by applying the coefficients to calculate features to use for the holdout group;
   comparing the features to use for the holdout group to the principal components for use in tuning the predictive model;
   tuning, by the one or more processors, the predictive model based on the comparing, wherein the tuning comprises machine learning, the machine learning comprises repeating various steps utilizing a data set with known information, to tune and improve accuracy of identifying common features in a given raw data set comprising peptide libraries of patients designated as either diagnosed or pre-diagnosed with a condition or not diagnosed with the condition based on identifying the common features in the data of the remaining groups, wherein the predictive model is configured to utilize the common features in the data of the remaining groups to determine a binary outcome for an individual, the various steps comprising:
      performing, by the one or more processors, a principal component analysis on the data set with the known information to identify common features in the data set with the known information;
      performing a cross-validation of the common features in the data set with the known information and the common features in the data of the remaining groups; and
      updating, by the one or more processors, the predictive model based on results of the cross-validation of the data set with the known information and the common features in the data of the remaining groups;
   obtaining, by the one or more processors, new raw data comprising a 12-mer peptide library of a given individual;
   applying, by the one or more processors, the predictive model to the new raw data to determine the binary outcome for the given individual; and
   providing, by the one or more processors, the binary outcome to the given individual, in real-time.

2. The computer-implemented method of claim 1, wherein applying the predictive model comprises performing a principal component analysis on the new raw data utilizing the coefficients and performing a logistic regression to generate the binary outcome.

3. The computer-implemented method of claim 1, wherein the peptide libraries comprise 12-mer peptide expressions of individuals.

4. The computer-implemented method of claim 1, wherein the condition comprises Stage I breast cancer.

5. The computer-implemented method of claim 1, wherein the segmenting comprises generating random numbers to select which record of the raw data set to assign to which of the groups.

6. The computer-implemented method of claim 3, comprising:
- prior to performing the principal component analysis, normalizing, by the one or more processors, peptides comprising the raw data set by adding peptide values of the peptides across all the peptides and dividing an expression values of each of the 12-mer peptide expressions by a resultant sum to compute a ratio.

7. The computer-implemented method of claim 1, wherein the cross-validation of the common features of each set of training data and the common features in the single training set is of a number of folds equal to a number of the remaining groups, to identify the principal components and determine the coefficients.

8. The computer-implemented method of claim 7, wherein the pre-defined level of validation accuracy is a highest validation accuracy based on the number of folds.

* * * * *